United States Patent [19]

Potin et al.

[11] 3,960,846

[45] June 1, 1976

[54] METHOD FOR PURIFYING LACTAMS

[75] Inventors: Philippe Potin; Michel Biensan, both of Billere, France

[73] Assignee: Ato Chimie, Courbevoie, France

[22] Filed: Sept. 20, 1974

[21] Appl. No.: 508,020

[30] Foreign Application Priority Data

Sept. 24, 1973 France ................. 73.34103

[52] U.S. Cl. ............... 260/239.3 A; 260/293.86;
260/326.5 FN; 23/252 R
[51] Int. Cl.² ....................... C07D 201/14
[58] Field of Search ............. 260/239.3 A

[56] References Cited
UNITED STATES PATENTS 3,154,540  10/1964  Beer et al. ............. 260/239.3 A

FOREIGN PATENTS OR APPLICATIONS 1,926,932  1/1970  Germany ............. 260/239.3 A

*Primary Examiner*—Natalie Trousof
*Assistant Examiner*—Robert T. Bond
*Attorney, Agent, or Firm*—Burgess Ryan and Wayne

[57] ABSTRACT

The instant invention relates to a method for purifying lactams wherein the lactam to be purified is contacted in the fused state with inorganic adsorption agents.

The said method comprises contacting the lactam to be purified in the fused state with an inorganic adsorbent, then separating the lactam from the adsorbent and regenerating said adsorbent if desired, wherein said adsorbent is impregnated with at least one impregnation compound selected from the group consisting of an acid and the alkali metal salts which are thermally stable and exert no action on the lactam at temperatures lower tha 250°C.

21 Claims, 2 Drawing Figures

METHOD FOR PURIFYING LACTAMS

The instant invention relates to a method for purifying lactams wherein the lactam to be purified is contacted in the fused state with inorganic adsorption agents.

The lactams, especially epsilon-caprolactam and lauryl-lactam, are important raw materials in the field for the production of polyamides, which are polymers the industrial applications of which are extremely varied, particularly in the field of manufacturing fibres, filaments and moulded articles.

These lactams obtained by various processes, and more particularly by the Beckmann transposition of corresponding alicyclic oximes, always contain a variable amount of impurities, the presence of which, even in the form of traces which are not revealed by analysis, results in a substantial decrease in the stability of the lactam during the period of storing, or in a substantial decrease of the quality of the polyamides obtained on the basis of said lactams.

Various methods for purifying lactams are already known. In accordance with one known method, the lactam in the fused state is contacted with an inorganic adsorption agent, especially alumina, silica, or silico-aluminate; the lactam is then separated from the adsorption agent, whereafter the latter may be regenerated.

This method which is easy to carry out from a technological point of view and allows the content of impurities of the lactam to be decreased in a substantial proportion, is nevertheless not entirely satisfactory in practice, as when contacted with the adsorption agent, the lactam partially forms oligomers the presence of which in the lactam is undesirable on account of the fact that said oligomers are detrimental to the quality of the finally obtained polyamide.

Research work which has led to the instant invention has provided a novel process for purifying lactams in the fused state by means of inorganic adsorbents, which method practically avoids the formation of oligomers when the lactam in the fused state is contacted with the adsorbent, whereby the drawbacks of the above-described known method are overcome.

It is an object of the instant invention to provide a method for purifying lactams comprising contacting the lactam to be purified in the fused state with an inorganic adsorbent, then separating the lactam from the adsorbent and regenerating said adsorbent if desired, wherein said adsorbent is impregnated with at least one compound selected from the group comprising an acid and the alkali metal salts which are thermally stable and exert no action on the lactam at temperatures lower than 250°C.

The acids or alkali metal salts which may be used as compounds for impregnating the adsorbent are inorganic or organic acids or alkali metal salts of said acids which, at temperatures lower than 250°C, are not subject to decomposition by heat and do not react with the lactam to be purified. Typical examples of such acids and salts which may advantageously be used are boric acid and phosphoric acid, sulphuric acid, alkali metal borates, phosphates and sulphates, especially sodium borate, sodium phosphate, sodium sulphate or potassium sulphate, and sodium chloride.

The amount of compound used for impregnating the adsorbent is widely variable depending on the nature of said compound, the nature of the adsorbent used and the nature of the lactam to be purified. Said amount may be advantageously comprised between 0.1 and 30% by weight of the adsorbent, and is preferably comprised between 1 and 20% by weight of said adsorbent.

The adsorption agents (or adsorbents) which are used after impregnation in accordance with the instant invention are generally selected from the group of the conventional inorganic adsorbents, especially from the group comprising silica and alumina, which adsorbents are used in the known adsorption processes; however other less conventional types of inorganic adsorbents, such as the apatites, may also be used. Preferably, alumina is used in the method according to the present invention, on account of its efficiency and its comparatively low cost.

The adsorbent agent may be impregnated with the selected acid or the alkali metal salt of said acid by any convenient known process. More particularly, the adsorbent agent which has been previously washed with water and dried may be intimately contacted with a solution of the acid or the salt in a convenient solvent, especially in water, then after separation of the impregnation solution and fast drying, the impregnated adsorbent agent may be subjected to a final drying operation with a view to eliminating the solvent subsisting in the pores of said adsorbent agent, without causing the decomposition of the acid or the salt.

The method according to the invention may be applied to the purification of lactams in general, and more particularly to lactams obtained by the Beckmann transposition of corresponding alicyclic oximes. The instant method allows particularly advantageous results to be achieved in the field of purification of lactams having a high melting point, such as the lauryl-lactam.

When carrying out the method according to the instant invention the lactam in the fused state is contacted with the selected impregnated adsorption agent, and after a sufficiently long contacting time the lactam is separated from the adsorbent.

To this end, the adsorbent may, e.g., be introduced into a melting container provided with agitating means and containing the fused lactam, whereafter the lactam is separated by filtering from the adsorbent. It is also possible to introduce the fused lactam in one or more columns containing the adsorbent, said columns being maintained at a convenient temperature so as to prevent the lactam from cooling and solidifying.

If it is desired, the adsorbent polluted by the impurities from the lactam may be regenerated, and then recirculated, said regeneration being carried out by a thermal treatment of the adsorbent at a convenient temperature for pyrolyzing the impurities which it contains, without causing the decomposition of the impregnation agent, or by a treatment of the adsorbent by means of convenient solvents, especially alcohols such as methanol, or halogenated hydrocarbons such as trichloroethylene, which dissolve said impurities without dissolving the impregnation agent, said treatment by means of solvents being preferably carried out under pressure.

The method according to the invention may be carried out in one step or a plurality of successive steps, it may also be carried out in an intermittent manner or a continuous manner. Said method may particularly be carried out downstream of the distillation operation effected in accordance with a conventional purification method. The amount of impregnated adsorbent required for purifying the lactam may vary within widely spread limits, depending on the initial amount of lactam and the nature of the process used. Said amount is generally comprised between 0.05 and 60% by weight of the lactam to be purified. When the method of the present invention is carried out in an intermittent manner, the amount of impregnated adsorbent to be used is comprised between 1 and 50% and preferably between 2 and 30% of the weight of lactam to be purified, whereas when said method is carried out in a continuous manner, especially by means of columns provided with adsorbent, the amount of impregnated adsorbent is comprised preferably between 0.1 and 15% of the weight of the lactam to be treated.

The temperature at which the method according to the instant invention is carried out must be at least equal to the melting point of the lactam to be purified, and it may vary within widely spread limits above said melting point. However, as the efficiency of the adsorbent decreases at elevated temperatures, it is preferable to operate at temperatures which do not exceed the melting point of the lactam by more than several tens of degrees, i.e., more than 80°.

The duration of the contact of the fused lactam with the adsorbent varies, inter alia, as a function of the nature of said adsorbent and as a function of its granulometric data (particle size). It is advantageous within the scope of the instant invention to operate with contact times comprised between 10 minutes and 10 hours; preferably, the contact time is comprised between 20 minutes and 6 hours.

When carrying out the method according to the instant invention, any device which allows a contact between a solid and a viscous liquid and allows a separation of said liquid from said solid may be used.

When the method is carried out in an intermittent manner (operation by successive batches) a melting container provided with an agitator may be used, the impregnated adsorbent being added to the fused lactam in said melting container and the latter being associated to a convenient filter.

In the case of semi-continuous or continuous operation a device may be used which comprises a melting container for melting the lactam, a metering pump arranged at the outlet of said melting container, one or more columns containing a convenient impregnated adsorbent, a first group of conduits provided with commutating valves of a convenient type for connecting the inlet of said column, or columns, to the outlet of said metering pump; a second group of conduits provided with convenient commutating valves for connecting the outlet of the column or columns to a receiving chamber adapted to receive the purified lactam, which receiving chamber may constitute the zone of polymerization of said lactam, means for maintaining a predetermined temperature in said column or columns, which means may be constituted by jackets surrounding said column or columns and wherein a fluid having a convenient temperature is circulated, said device also comprising, if desired, means for actuating the various commutating valves in accordance with a predetermined sequence, said means being constituted by a clock or similar time base device.

In a particularly advantageous embodiment the device for carrying out the method according to the invention also comprises a circuit for regenerating the adsorbent, which circuit comprises a chamber containing fresh regeneration liquid and connected to the inlet of the column or columns through said first group of conduits, as well as a recovering chamber for recovering the regeneration liquid after the regeneration has been carried out, said recovering chamber being connected to the outlet of said column or columns through said second group of conduits.

The above and other features and advantages of the instant invention will become apparent from the description hereinbelow which refers to the appended drawings showing various embodiments of the instant invention by way of example, without limiting the scope of the invention thereto.

Figure 1:
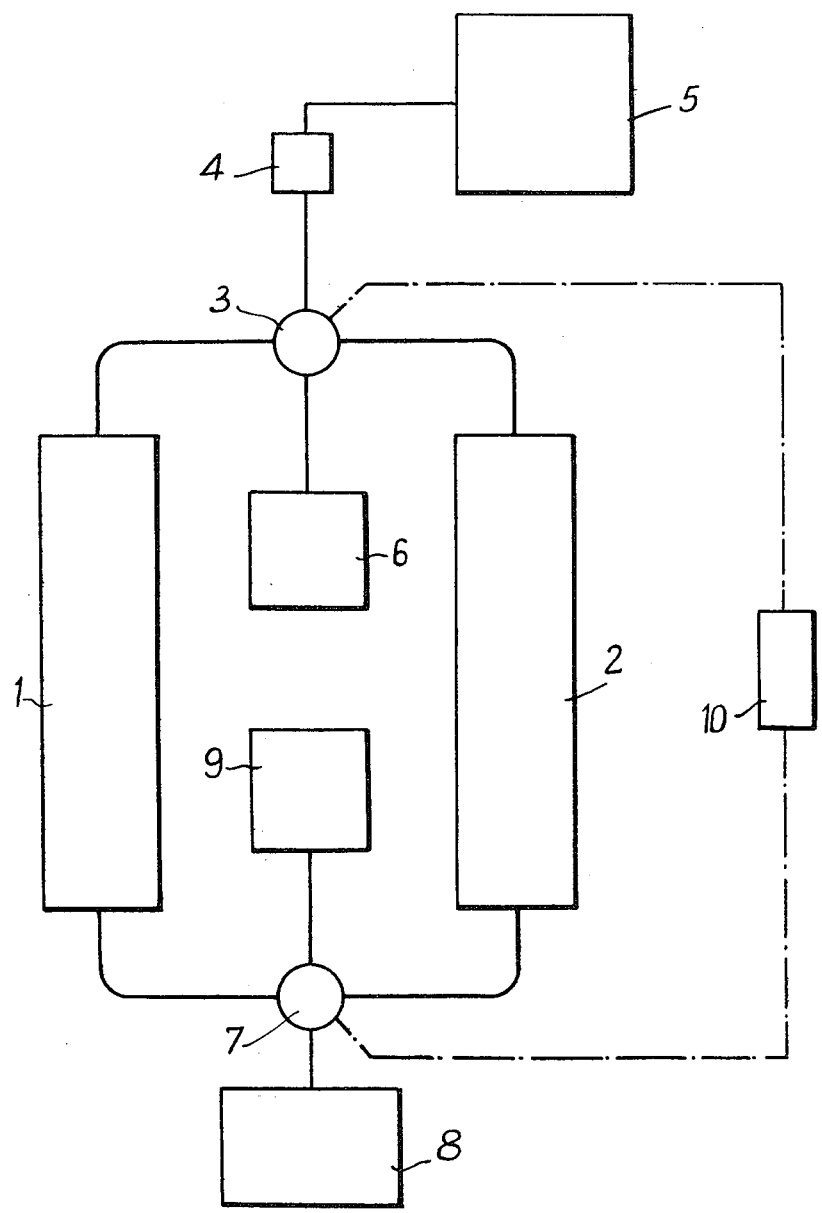
FIG. 1 is a schematic view of a device for carrying out the method of the instant invention, said device comprising a regeneration circuit and being adapted to operate in a continuous manner.

The device shown in FIG. 1 comprises two columns, 1, 2 containing impregnated adsorbent, each column having a jacket (not shown) for circulating a fluid having a predetermined temperature. The respective inlets of said columns are connected by a first group of conduits provided with a commutation valve 3 selectively to the outlet of a metering pump 4 arranged at the outlet of a melting container 5 for the lactam and to a chamber 6 containing a regeneration liquid constituted, for example, by methanol or trichlorethylene. The second group of conduits, provided with a second commutation valve 7, connects the respective outlets of columns 1 and 2 alternatively to a chamber 8 adapted to receive the purified lactam, and to a chamber 9 adapted to collect the regeneration solvent which has been used to regenerate the adsorbent. The solvent is then purified and recycled into chamber 6 containing the fresh regeneration liquid. The commutation of valves 3 and 7 is controlled by a clock 10 in such a manner that one of the columns is connected to the metering pump arranged at the outlet of the melting container, and is also connected to the chamber receiving the purified lactam, whereas the other column is connected to chamber 6 containing fresh solvent for the regeneration of the adsorbent, said other column being also connected simultaneously to chamber 9 adapted to receive the polluted regeneration liquid.

The device described hereinabove operates as described hereinafter:

At a given time, column 1 is operating in the adsorption phase, while column 2 is operating in the regeneration phase. The fused lactam from regenerator 5 is injected into column 1 by metering pump 4 through commutation valve 3, while the purified lactam flows through said column towards receiving chamber 8 through commutation valve 7. At the same time column 2 operating in the regeneration phase receives the regeneration agent from chamber 6 through valve 3, said regeneration liquid being polluted, i.e. charged with impurities, while flowing through said column 2. The polluted regeneration liquid flows into chamber 9 through valve 7. When the regeneration in column 2 has been accomplished to a satisfactory degree, clock 10 causes the position of valves 3 and 7 to be reversed, so that column 2 starts operating in the adsorption phase, while column 1 starts operating in the regeneration phase.

Figure 2:
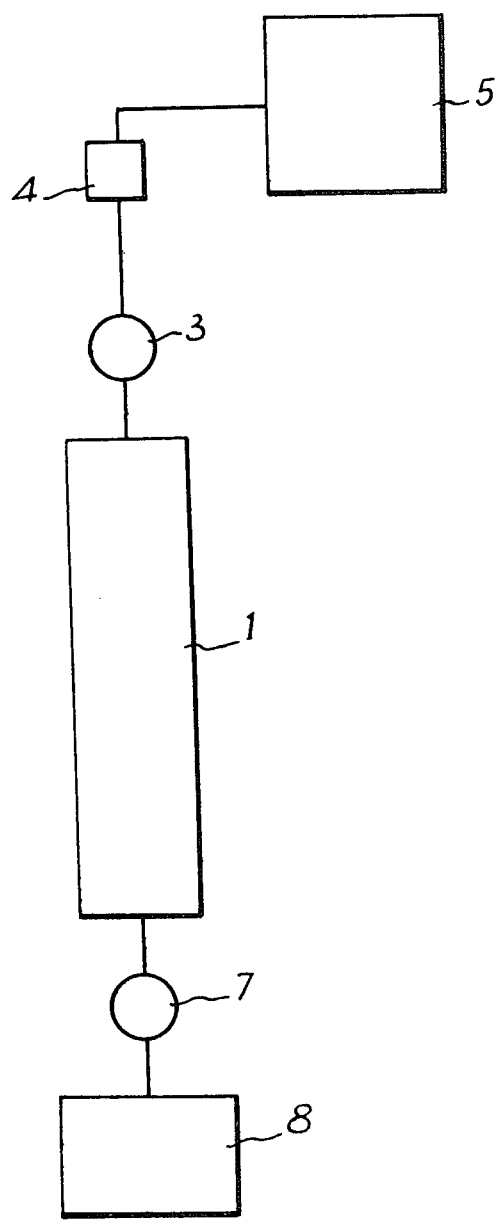
FIG. 2 is a schematic view of the device for carrying out the method according to the invention in a semi-continuous manner.

When the lactam is to be treated in a semi-continuous manner, a less elaborate device such as the one shown in FIG. 2 may be used. This device is not provided with a regeneration circuit and comprises only one column provided with the impregnated adsorbent. In this embodiment the device comprises substantially a melting container 5 at the outlet of which is arranged a metering pump 4 which is connected to the inlet of a column 1, a commutating valve 3 being interposed, if desired, between metering pump 4 and column 1; the outlet of column 1 is connected to a chamber 8 adapted to receive the purified lactam, and a commutating valve 7 is interposed, if desired, between the outlet of column 1 and the above-mentioned chamber 8.

When the method according to the instant invention is carried out in an intermittent or semi-continuous manner, the polluted adsorbent may be regenerated in a complementary device which may be constituted by a reactor provided with agitating means and adapted to effect the regeneration by treating the adsorbent with a regeneration liquid. Said complementary device may also be constituted by an auxiliary oven wherein the regeneration is effected by pyrolysis of the impurities.

The examples hereinbelow illustrate the invention, but are not to be construed as limiting the scope thereof.

EXAMPLE 1

Various test series relating to the purification of lauryl-lactam have been carried out, using adsorbents which were constituted by commercially available alumina having a particle size of 200–600 microns, said alumina being impregnated, respectively, with the following compounds: sulphuric acid, orthophosphoric acid, orthoboric acid, sodium chloride, and borax ($Na_2B_4O_7$).

The impregnated alumina was prepared as follows:

The dried alumina was treated with an aqueous solution of the selected acid or salt, said treatment being effected by adding to the alumina, while agitating the same, small fractions of a 10% solution of the acid, or by adding to said alumina a sufficient volume of a solution having a predetermined concentration with a view to slightly coating the alumina with the solution. After rapid drying and homogenisation by agitation, the impregnated alumina was submitted to a final drying operation at 130°C under a vacuum of 1 Torr during 3 hours.

The purification of the lactam was effected in a tubular melting container having an inner diameter of 40 mm, wherein 20 grs of the impregnated alumina and 100 grs of lauryl-lactam were introduced. The lactam was melted and the mixture was maintained at a temperature of 200°C during 3 hours while the mixture was agitated sufficiently so as to maintain the alumina in suspension, this phase of the treatment being effected in a nitrogen atmosphere.

The fused lactam was then separated from the alumina by filtering, whereafter samples of the thus obtained lactam were submitted, after cooling, to an analysis with a view to determine their oligomer content and their degree of purity.

The oligomer content of the lactam was determined as described hereinbelow:

The sample of purified lactam was introduced into a volume of chloroform corresponding to 10 ml of chloroform per gram of lactam; after 15 hours of dissolution the insoluble substances, i.e. the oligomers, were filtered and weighed. The oligomer contents were then determined by relating the weight of the insoluble substances to the weight of dissolved lactam.

The purity of the lactam was determined by means of two tests; i.e. the so-called potassium hydroxide test and the so-called polymer coloration test, which were carried out as described hereinbelow:

Potassium hydroxide test 10 grs of lactam and 0.1 gr of potassium hydroxide were introduced into a Pyrex glass tube having an inner diameter of 13 mm and an outer diameter of 15 mm. The tube was sealed in a nitrogen atmosphere and immersed in a bath at 170°C for 10 minutes with intermittent agitation. The coloration which appeared was then measured by comparison with the GARDNER scale, utilizing a LOVIBOND comparator.

Polymer coloration test 10 grs of lactam were introduced into a tube having an inner diameter of 13 mm and an outer diameter of 15 mm; the content of the tube was submitted to a nitrogen stream. The tube was then immersed in a bath having a temperature of 250°C, and after the fusion of the lactam 0.05 gr of sodium hydride were added and dispersed by nitrogen bubbling. The content of the tube was then maintained at 250°C in a nitrogen atmosphere during 30 minutes. The coloration of the thus obtained polymer was then determined as described hereinabove with reference to the potassium hydroxide test, by comparison with the GARDNER scale.

The specific operating conditions and the results obtained are listed in Table 1 hereinbelow. The results obtained in Table 1 show that the utilisation of an impregnated solvent in accordance with the instant invention allows to reduce to acceptable values the oligomer content of the purified lactam, without affecting the purity of the obtained lactam by the presence of the compound used for impregnating the adsorbent.

TABLE I

| Impregnation Agent | Amount of impregnation agent (% of weight of lactam) | Oligomer content (%) | Purity of the lactam* (GARDNER scale) | |
|---|---|---|---|---|
| | | | potassium hydroxide test | polymer coloration |
| Nil | | 25 | 0 | |
| $H_2SO_4$ | 1 | 2,75 | 0 | 1 |
| | 6 | 2,62 | | |
| | 10 | 1,90 | | |
| | 20 | 2,90 | | |
| $H_3PO_4$ | 18,40 | | 0 | 1 |
| | 4 | | | |
| | 8 | 2,45 | | |
| | 10 | 2,60 | | |
| | 15 | 1,40 | | |
| | 20 | 0,88 | | |
| $H_3BO_3$ | 2 | 2,83 | 0 | 1 |
| | 4 | | | |
| | 6 | 1,26 | | |
| | 10 | 1,65 | | |
| | 15 | 1,18 | | |
| | 20 | 1,01 | | |
| NaCl | 4 | 1,53 | 0 | 1 |
| $Na_2B_4O_7$ | 4 | 1,72 | 0 | 1 |

*The purity of the non-treated lactam, espressed in units of the GARDNER scale, is 5 when determined by the potassium hydroxide test, and 8 when determined by the polymer coloration test.

EXAMPLE 2

A series of purification tests of lauryl-lactam have been carried out in a continuous manner, using a device constituted by a melting container at the outlet of which was arranged a metering pump connected to the inlet of a column containing (a) alumina impregnated, respectively, with phosphoric acid and orthoboric acid, or (b) non-impregnated alumina, while the outlet of said column was connected to a chamber provided with a nitrogen atmosphere and adapted to receive the purified lactam.

The fused lactam was injected into the column from the bottom toward the top thereof, at flow rates which were controlled by the metering pump, and the temperature of said column was maintained at 180°C by circulating steam in a jacket surrounding said column.

During these tests, samples of the purified lactam issuing from the column were taken at predetermined time intervals determined by the time origine corresponding to the moment when the lactam started to issue from the column, and the oligomer content of said samples was determined as described in Example 1.

A dwelling or contact time of the lactam contacted with the adsorbent equal to the time necessary for a weight of lactam equal to the weight of adsorbent contained in said column to flow through said column was also determined.

The specific operating conditions and the results obtained are listed in Table II herein below.

When a non-impregnated adsorbent, constituted in the present instance by alumina, is used the oligomer content is comparatively high and increases with the duration of utilisation of the adsorbent.

In contrast thereto, when the purification of the lactam is effected by means of an impregnated adsorbent according to the present invention, this adsorbent being in the present instance constituted by impregnated alumina, the oligomer content is extremely low and remains at an acceptable level even after very long periods of utilisation, which could not be envisaged if non-impregnated adsorbents were used.

TABLE II

| Impregnation Agent | Amount of agent (% of weight of adsorbent) | Dwelling time | Sampling time (in hours from time origin) | Oligomers content (%) |
|---|---|---|---|---|
| Nil | | 2H40min | 1 | 3,03 |
| | | | 24 | 6,60 |
| $H_3PO_4$ | 4 | 2H30min | 3 | 0 |
| | | | 44 | 0,77 |
| | | | 72 | 1,40 |
| $H_3BO_3$ | 4 | 2H20min | 3 | 0 |
| | | | 17 | 0 |
| | | | 24 | 0,9 |
| $H_3BO_3$ | 10 | 2H50min | 18 | 0 |
| | | | 22 | 0 |
| | | | 45 | 0,03 |
| | | | 70 | 0,41 |
| | | | 93 | |

What is claimed is:

1. A method of purifying a lactam obtained by the Beckmann transposition of the corresponding alicyclic oximes, comprising the steps of:
   a. contacting said lactam to be purified in the fused state with at least one inorganic adsorbent selected from the group consisting of alumina, silica, and an apatite, said adsorbent having been impregnated with at least one compound selected from the group consisting of an acid and the corresponding alkali metal salts thereof which are thermally stable and non-reactive with the lactam at a temperature lower than 250°C, and
   b. separating the purified lactam from the adsorbent, the aforesaid steps being carried out at a temperature which is at least equal to the melting point of the lactam and said lactam is maintained in the fused state during the purification procedure.

2. A method for purifying a lactam according to claim 1 in which the adsorbent obtained after the separation of the purified lactam is regenerated.

3. A method according to claim 1 wherein said purification is effected in an atmosphere of nitrogen.

4. A method according to claim 1 wherein said lactam to be purified is allowed to come in contact with said inorganic adsorbent for a period between 10 minutes and 10 hours.

5. A method according to claim 1 wherein said contacting time varies between 20 minutes to 6 hours.

6. A method according to claim 1, wherein said compound for impregnating the adsorbent is a member selected from the group consisting of boric acid, phosphoric acid, sulphuric acid, and the corresponding alkali metal salts of these acids, and sodium chloride.

7. A method according to claim 1 wherein said adsorbent is impregnated with 0.1 to 30% by weight of said compound based on the weight of said adsorbent.

8. A method according to claim 1 wherein said adsorbent is impregnated with 1 to 20% by weight of said compound based on the weight of said adsorbent.

9. A method according to claim 1 wherein said impregnated adsorbent contacted by said lactam is in an amount of 0.05 to 60% based on the weight of said lactam to be purified.

10. A method according to claim 1 wherein said lactam is in contact with said adsorbent at a temperature which exceeds the melting point of said lactam.

11. A method according to claim 9 wherein the lactam is in contact batchwise or in an intermittent manner, with said adsorbent.

12. A method according to claim 11 wherein the quantity of the adsorbent is between 1 and 50% by weight of said lactam.

13. A method according to claim 12 wherein the quantity of the adsorbent is between 2 and 30% by weight of said lactam.

14. A method according to claim 9 wherein the lactam is in continuous contact with said adsorbent.

15. A method according to claim 14 wherein the quantity of the impregnated adsorbent is between 0.1 and 50% by weight of the lactam.

16. A method according to claim 2 wherein said regeneration of said adsorbent is effected by heating said adsorbent at a temperature below the decomposition temperature of said impregnated compound.

17. A method according to claim 2 wherein said adsorbent is regenerated by treating said adsorbent with a solvent selected from the group consisting of an alcohol and a halogenated hydrocarbon.

18. A method according to claim 17 wherein said alcohol is methanol.

19. A method according to claim 17 wherein said halogenated hydrocarbon is trichlorethylene.

20. A method according to claim 1 wherein said adsorbent is alumina.

21. A method according to claim 1 wherein said lactam to be purified is lauryl-lactam.

* * * * *

UNITED STATES PATENT OFFICE
CERTIFICATE OF CORRECTION

Patent No. 3,960,846          Dated     June 1, 1976

Inventor(s)    Philippe Potin, et al

It is certified that error appears in the above-identified patent and that said Letters Patent are hereby corrected as shown below:

In the Abstract of the Disclosure: the last line, change "tha" to --than--.

Column 6, line 54: --18,40-- should be set forth in the "Oligomer content (%)" column; --1-- should be inserted in the "Amount of impregnation ..." column, in place of "18,40".

Column 8, line 29: Change "claim 1" to --claim 7--.

Signed and Sealed this

Ninth Day of November 1976

[SEAL]

Attest:

RUTH C. MASON
Attesting Officer

C. MARSHALL DANN
Commissioner of Patents and Trademarks